United States Patent [19]

Wong et al.

[11] Patent Number: 5,463,223
[45] Date of Patent: Oct. 31, 1995

[54] DISPOSABLE ALL PURPOSE MICRO SAMPLE HOLDER

[75] Inventors: Mag K. Wong; Patrick T. T. Wong, both of Ottawa, Canada

[73] Assignee: Patwong Technologies, Inc., Ottawa, Canada

[21] Appl. No.: 185,456

[22] Filed: Jan. 24, 1994

[51] Int. Cl.⁶ .................................................. G01N 21/01
[52] U.S. Cl. ............................... 250/339.12; 250/339.07; 250/339.08
[58] Field of Search .................. 250/339.12, 339.08, 250/339.07, 339.06; 356/244

[56] References Cited

U.S. PATENT DOCUMENTS

| | | | |
|---|---|---|---|
| 2,533,089 | 12/1950 | Brewer et al. | 435/287 |
| 3,521,963 | 7/1970 | Bader | 356/244 |
| 3,630,849 | 12/1971 | Land | 435/298 |
| 4,678,913 | 7/1987 | Dodd et al. | 250/339.05 |
| 4,775,628 | 10/1988 | Takakura et al. | 435/298 |
| 4,979,332 | 12/1990 | Nagaya et al. | 47/69 |
| 4,980,551 | 12/1990 | Wong | 250/338.1 |
| 5,003,174 | 3/1991 | Däwyler et al. | 250/343 |
| 5,038,039 | 8/1991 | Wong et al. | 250/339.12 |
| 5,057,691 | 10/1991 | Kaihara et al. | 250/339.11 |
| 5,124,555 | 6/1992 | Härtl | 250/373 |
| 5,168,162 | 12/1992 | Wong et al. | 250/339.12 |
| 5,290,705 | 3/1994 | Davis | 436/164 |

FOREIGN PATENT DOCUMENTS 4-155245   5/1992   Japan ................................. 356/244

OTHER PUBLICATIONS

Enzo Benedetti et al., "Analytical Infrared Spectral Differences Between Human Normal and Leukaemic Cells (CLL)–I" *Leukemia Research* vol. 8, No. 3 pp. 483–489, (1984).

Enzo Benedetti et al. "New Possibilities of Research in Chronic Lymphatic Leukemia by Means of Fourier Transform–Infrared Spectroscopy–II", *Leukemia Research*, vol. 9, No. 8, pp. 1001–1008, (1985).

*Primary Examiner*—Constantine Hannaher
*Attorney, Agent, or Firm*—Cohen, Pontani, Lieberman, Pavane

[57] ABSTRACT

A disposable all purpose micro sample holder comprised of a thin rigid plate-shaped frame, substantially opaque to infrared light, having a bore extending therethrough in or over which is mounted an optical window made of a material substantially transparent to infrared light. An optional flexible film is sized, shaped and affixed to the upper surface of the frame to completely cover the bore in the frame. The film is substantially transparent to the frequencies of the infrared light to be used. A sample is placed on optical window over the bore and beneath the film. For powder or solid samples, two sample holders, without the film, are releasably clamped together.

20 Claims, 8 Drawing Sheets

DISPOSABLE ALL PURPOSE MICRO SAMPLE HOLDER

FIELD OF THE INVENTION

The present invention relates to sample holders for use in infrared spectroscopy of biological, organic and inorganic samples.

BACKGROUND OF THE INVENTION

As disclosed in U.S. Pat. Nos. 5,038,039 and 5,168,162, which are incorporated herein by reference, infrared spectroscopy may be used to detect anomalies in samples of biological tissues and cells in natural and cultured form. A beam of infrared light is directed at the sample, and any anomalies in the sample are detected by analyzing the changes in the infrared absorption within one or more frequency ranges. The change in absorption may evidence itself as a change in absorption intensity at one or more particular frequency absorption peaks, a change in frequency at which one or more absorption peaks occur, the appearance of one or more new absorption peaks at new frequencies, or a combination of two or three of these phenomena. The infrared spectroscopy may be performed at atmospheric pressure or at an elevated pressure. The sample may comprise cells, secretions, exudates, transudates, bacteria, scrapings, brushings or other kinds of exfoliated cells from various organs, tissues or growths including tissue slices, mashed cells, or cells dispersed or suspended in water or other liquids. By using these infrared spectroscopy methods, anomalies such as malignancies and certain diseases, such as diabetes, cirrhosis and arthritis, can be reliably detected at an early stage in their development by persons with little or no medical training. In fact, because the disclosed methods provide numerical results in the form of intensity as a function of frequency, no significant subjective interpretation is required. Consequently, the analysis of samples may be entirely automated and/or computerized, thereby primarily requiring human involvement only in the initial obtaining and preparation of samples for infrared spectral analysis.

Infrared analysis of biological samples is also disclosed in the articles authored by Benedetti et al. in Leukemia Research, Vol. 8, No. 3, pp. 483–489 (1984) and in Leukemia Research, Vol. 9, No. 8, pp. 1001–1008 (1985).

In order to conduct such infrared spectroscopy of such samples, it is typically necessary to mount the sample in some kind of sample holder which has an optical window substantially transparent to the infrared light to be used, which ensures that the infrared light is not completely absorbed by the sample, and which substantially eliminates infrared interference fringes created by the sample which might obscure the sample's infrared absorption spectrum.

An sample holder that may be used at atmospheric pressure in conjunction with the infrared spectroscopy methods described above is disclosed in U.S. Pat. No. 4,980,551, which is incorporated herein by reference. The disclosed sample holder comprises a frame having a passage extending therethrough, and a pair of juxtaposed infrared transparent optical windows disposed within the passage. At least one of the optical windows has a recess formed in the surface abutting the other optical window into which a sample is placed. The sample holder also includes a mask that restricts the infrared light to the recess formed in the optical windows and a means to urge the two optical windows into contact with one another, thereby also clamping the sample within the recess(es). The shape of the recess(es) in the optical window(s) provides paths of propagation of adjacent infrared light rays that are different in length, thereby substantially eliminating interference fringes in the infrared spectra of the sample and clarifying the infrared absorption spectra of the sample being analyzed. The sample holder is useful for examining organ tissue or other deformable semi-solid material, such as, for example, gels, amorphous polymers and highly viscous liquid. Although this sample holder is reliable, functional and useful for many applications, it has certain disadvantages. In particular, after a sample is placed in the recess between the two optical windows, the sample holder must be assembled by mounting and securing the two optical windows into the frame. This assembly process is time consuming and difficult, thereby detracting from the benefits of the infrared spectroscopic analytical method. Additionally, the size of the optical windows in the sample holder is larger than absolutely necessary. Because the infrared absorption spectra is obtained based upon the light that travels through the sample and the optical windows in line therewith, i.e., the portions of the optical windows above and below the recess(es) in the optical window(s), the remaining portions of the optical windows are not needed, as evidenced by the fact that those excess portions of the optical windows are masked. The optical windows are typically the most expensive elements of the sample holder because the material comprising the optical windows is typically expensive and because the optical windows are typically difficult and therefore expensive to fabricate. As a consequence, the inclusion of this excess portion of optical window increases the cost of the sample holder making it unsuitable as a single use, disposable sample holder. The excess portions of the optical windows also make the sample holder less suitable for use in applications where a pressure is to be applied to the sample since a pressure might fracture the optical windows. Additionally, the sample holder typically must be cleaned for reuse, thereby creating a contamination risk, both to the technical personnel involved in the cleaning procedures and to the work environment, and also generating an expensive and logistically difficult problem associated with the safe disposal of the contaminated cleaning agents used in the cleaning procedures.

A sample holder that may be used at high-pressures in conjunction with the above described infrared spectroscopy methods is disclosed in U.S. Pat. No. 4,970,396, which is incorporated herein by reference. This sample holder comprises a frame or gasket made of a high compressive strength material having a passage passing therethrough, and an infrared transparent optical window disposed in the passage. The optical window is sized and shaped so as to form a recess between the upper surface of the optical window and the upper surface of the frame or gasket. A sample can be placed into this recess. As was the case with the above described atmospheric pressure sample holder, the shape of the recess in this sample holder provides paths of propagation of adjacent infrared rays that are different in length to substantially eliminate infrared interference fringes to clarify the infrared absorption spectra. Pressure is applied to the bottom surface of the window and to the sample by anvils which are preferably comprised of diamond crystals. The sample is sealed into the recess of the sample holder when the diamond anvils are pressed into contact with the frame or gasket. This high pressure sample holder is useful for examining liquids, solids, aqueous systems and aqueous biological systems and lipids, proteins, nucleic acids, hydrocarbons and animal or vegetable tissue (alive or dead) and bacteria. Although this sample holder is also reliable, functional and useful for many applications, it also has certain disadvantages. In particular, the anvils are extremely expensive, because the diamonds of which they are comprised are inherently expensive. Fabrication and assembly costs of the sample holder are high because the anvils must be cut and precisely oriented in the sample holder so that the anvil surfaces adjacent to the optical window are parallel to one another within a tolerance of one interference fringe for the particular frequency of light being used in the interferometer. Additionally, because the optical path of the diamond anvils is relatively small (less than about 0.5 mm.), in order to obtain reasonably acceptable infrared spectra, it is highly desirable to use a light beam condenser and a highly sensitive infrared detector. As a consequence of using these supplementary elements, proper optical alignment among the elements and the sample is difficult to obtain. The disclosed sample holder also cannot be used to obtain infrared spectra at atmospheric pressure. Finally, because of the relatively high cost associated with manufacturing this particular sample holder, it is not suitable as a single use, disposable sample holder, but must be cleaned for reuse thereby creating the contamination and disposal problems discussed above.

SUMMARY OF THE INVENTION

The disposable all purpose micro sample holder of the present invention is useful in the spectroanalysis of any kind of biological, organic or inorganic sample, including, for example, cells, secretions, exudates, transudates, bacteria, lipids, proteins, nucleic acids, hydrocarbons, scrapings, brushings or other kinds of exfoliated cells from various organs, animal or vegetable tissues or growths including tissue slices, mashed cells, or cells dispersed or suspended in water or other liquids, or organic or inorganic compounds. Furthermore, the sample holder of the present invention can accommodate a sample in any physical form, including, for example, liquids, solutions, solid suspensions, dispersions, emulsions, aqueous systems and aqueous biological systems, solids, powders, crystals and deformable semi-solid material, such as, for example, gels, amorphous polymers and highly viscous liquids.

The design of the sample holder of the present invention which incorporates a relatively small optical window, makes it particularly inexpensive and thus suitable as a single use, disposable sample holder, thereby eliminating the contamination and disposal problems discussed above associated with cleaning sample holders for reuse. Additionally, the sample holder of the present invention requires minimal assembly which significantly simplifies its use, thereby making the overall infrared spectroanalysis technique significantly more attractive as a diagnostic tool. The sample holder of the present invention is able to provide high resolution, high quality infrared spectra with substantially no noise caused by infrared interference fringes or other sources.

The sample holder of the present invention is comprised of a frame which is a relatively thin rigid plate having a size and shape so that it can be appropriately inserted into or otherwise mounted for use with an infrared spectrophotometer. The frame is preferably made of any inexpensive, easily machinable or moldable, rigid material so that the frame is substantially opaque to the infrared light to be used by the spectrophotometer, is substantially insoluble in organic solvents, and is substantially unreactive to the sample that is to be analyzed. A bore extends through the frame and is preferably of a size to minimize the size of an optical window which is preferably mounted therein. A shoulder is preferably formed within the bore and serves as a mounting surface for the optical window.

The optical window is mounted within the bore so that the optical window is flush with the upper surface of the frame. Alternatively, the optical window may be mounted within the bore so as to form a recess between the optical window and the upper surface of the frame, or the optical window may be mounted onto the upper surface of the frame so as to cover the bore. The optical window is made of a material that is substantially transparent to the particular frequencies of the infrared light to be used in the spectroanalysis and can be made from a block of solid material or from a powder of a soft material which, when compressed, with or without the application of heat, forms a solid block. If the optical window is formed from a hard solid material, the optical window is sized so that it will fit tightly within the bore of the frame and remain in place by friction. Alternatively, an adhesive or sealer is used to affix the optical window to the shoulder and/or to the sides of the bore and to ensure that the optical window provides a fluid-tight seal so that liquid containing samples can be analyzed. If the optical window is made from a powder of a soft material, the optical window may be molded into the appropriate shape and then inserted into and/or affixed to the frame, or introduced as a powder into the bore and then compressed. The upper surface of the optical window forming the bottom of the recess is preferably planar or flat.

A flexible film is preferably affixed along one of its edges to the upper surface of the frame. The film is sized and shaped so that it completely covers the bore in the frame and the optical window. The film is made of a material that has a relatively low index of refraction and that is substantially transparent to the infrared light to be used. The thickness of the film is such that the film is flexible and such that interference fringes produced when the film is exposed to the infrared light generated by the spectrophotometer are weak and have a wavelength substantially higher than the infrared absorption bands of the samples analyzed. The film need not be attached to the frame but may be applied manually, with or without an adhesive, when or if needed. If the film is not to be used at all, the upper surface of the optical window is tapered, randomly scratched or has a concave or cone shaped indentation therein to substantially eliminate infrared interference fringes of the sample being analyzed.

In use, after a sample has been placed onto the optical window or into the recess formed above the optical window, the film is pressed down manually to contact the sample, thereby sealing the sample into the holder and, because of its uneven surface contour, also causing the paths of propagation of adjacent infrared light rays to have different lengths, thereby substantially eliminating interference fringes in the infrared spectra of the sample and significantly clarifying the infrared absorption spectra of the sample being analyzed. For a soft and/or malleable sample, the thickness or shape of the sample can manually adjusted by depressing the film and thereby the sample.

For a powder or solid sample, two sample holders of the present invention can be clamped together and no film is required. In this embodiment of the present invention, the optical windows are preferably flush with the surfaces of their respective frames. One of the contacting surfaces of the two frames of the sample holders is preferably tapered. Prior to clamping the sample holders together, the powdered or solid sample is placed onto the optical window of one of the two sample holders. By varying the clamping pressure, the thickness of the sample and/or the relative orientation of the two optical windows may be changed to substantially eliminate interference fringes during infrared analysis of the sample. Consequently, the double sample holder can be used to determine the pressure dependencies of the infrared absorption spectra of a sample. Alternatively, the optical window of one or both of the two sample holders may mounted on the surfaces of their respective frames, or within the bores of their respective flames so as to form a recess into which a sample is mounted. By properly selecting the positions and/or the thicknesses of the two optical windows, the size of any sample recess formed will preferably be such that the two optical windows will exert pressure upon the sample when the two sample holders are clamped together.

The disposable all purpose micro sample holder of the present invention can be used in conjunction with infrared spectroanalysis using near to extreme infrared light, frequencies from about 10 to about 10,000 $cm^{-1}$ (wavelengths about 1 to about 1000 µm.), depending upon the particular material comprising the optical window.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

DETAILED DESCRIPTION OF THE PREFERRED EMBODIMENTS

Figure 1A:
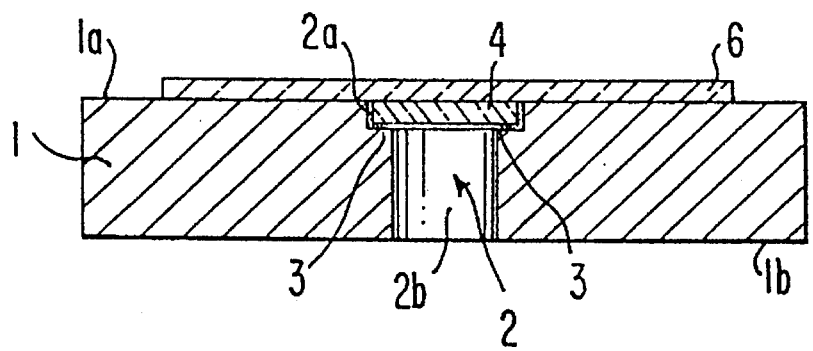
FIG. 1A is a cross-sectional side view of a first embodiment of the disposable all purpose micro sample holder of the present invention.
Figure 1B:
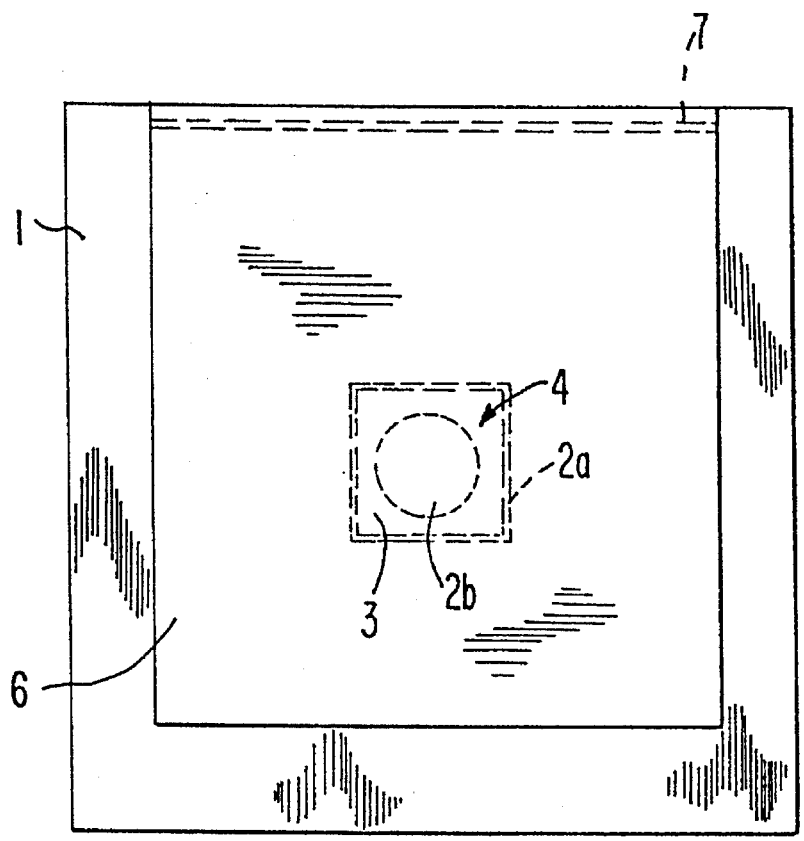
FIG. 1B is a top view of the embodiment of the present invention shown in FIG, 1A.

Referring to FIGS. 1A and 1B in which a first embodiment of the disposable all purpose micro sample holder of the present invention is shown in a cross-sectional side view and a top view, respectively, the sample holder is comprised of a frame 1 which is a relatively thin plate and can be of any size or shape, provided that it can be appropriately inserted into or otherwise mounted on the optical cell holder in the sample compartment of the particular infrared spectrophotometer to be used. Alternatively, the frame 1 of the sample holder may be sized and shaped to replace the optical window of a conventional optical cell. The frame 1 has a bore 2 extending from the upper surface 1a of the frame 1 to the lower surface 1b of the frame 1. The bore 2 is preferably circular in cross-section, although the bore 2 may have other cross-sectional shapes such as, for example, square or rectangular. The size of the bore 2 is minimized to reduce the size of the optical window 4, thereby reducing the cost of the entire sample holder. When a circular bore 2 is used, it is preferably from about 1 to about 5 mm. in diameter, while a square bore 2 is preferably from about 1 mm. to about 5 mm. on a side. The diameter of the bore 2 will depend upon the sensitivity of the particular spectrophotometer to be used so that a relatively insensitive spectrophotometer would require a relatively large diameter bore 2. The frame 1 is preferably made so that it is rigid, substantially opaque to the infrared light to be used by the spectrophotometer, substantially insoluble in organic solvents, and substantially unreactive to the sample that is to be analyzed. Additionally, the material comprising the frame 1 should preferably be relatively inexpensive and relatively easy to mold, cut and/or mill, thereby minimizing the overall cost of the entire sample holder. The frame 1 is thus preferably comprised, for example, of rigid paper board, rigid plastic, such as polypropylene, mineral filled polypropylene or high impact polystyrene, fiberglass reinforced plastic or a metal, such as aluminum or stainless steel. The frame 1 may optionally be coated with a material that gives the frame 1 its required opacity, unreactivity and/or stiffness. For example, if the frame is comprised of paper board, a plastic coating, with or without appropriate dyes, paints, enamels, coloring agents and/or opacifiers, may be applied to or incorporated into the paper board. The thickness of the frame 1 should be such that the frame 1 is sufficiently rigid so that the sample holder can be inserted or otherwise mounted into the spectrophotometer without deformation so that the optical window 4 will not be damaged while mounting the sample holder into the spectrophotometer. Thus, the thickness of the frame 1 is preferably between about 1.5 mm. and about 2.5 mm. A shoulder 3 is preferably formed within the bore 2 of frame 1 proximate to the upper surface 1a of the frame 1. The shoulder 3 reduces the diameter of the lower section 2b of the bore 2 so that the optical window 4 can be mounted and secured within the upper section 2a of the bore 2. As shown in the top view of FIG. 1B, the upper section 2a of the bore 2 is preferably square shaped. Although the shoulder 3 is shown in FIG. 1A as being stepped, the shoulder 3 may alternatively be wedge-shaped or tapered so that the diameter of the bore 2 reduces gradually toward the lower surface 1b of the frame 1. In the embodiment shown in FIGS. 1A and 1B, the upper section 2a of the bore 2 preferably extends downward from the upper surface 1a of frame 1 to a depth of from about 20 µm. to about 2.5 mm, preferably about 20 µm.

An optical window 4 is mounted in the upper section 2a of the bore 2 of the frame 1 on the shoulder 3 and preferably has a thickness so that the upper surface of the optical window 4 is substantially flush with the upper surface 1a of the frame 1. Thus, if the upper section 2a of the bore 2 is about 20 µm. deep, the optical window 4 is about 20 µm. thick. The thickness of the optical window 4 is preferably minimized to reduce the cost of the sample holder but must be such that the optical window 4 is substantially transparent to the infrared light to be used in the spectrophotometer, provides substantially no interference to this infrared light, and is not overly fragile. The thickness of the optical window 4 depends upon the composition of the optical window 4 and is illustratively between about 20 µm. and about 2.5 mm, preferably about 20 µm. The optical window 4 is fabricated of a material that is substantially transparent to the particular frequencies of the infrared light to be used in the spectrophotometer, i.e., near to extreme infrared light, frequencies from about 10 to about 10,000 cm$^{-1}$ (wavelengths from about 1 to about 1000 µm.). The optical window 4 can be made from a block of solid material or from a powder of a soft material which, when compressed, with or without the application of heat, forms a solid block. The optical window 4 is preferably made from any one of the following substances: AgBr, AgCl, BaF$_2$, CaF$_2$, CsBr, CsI, Ge, KBr, KCl, LiF, MgF$_2$, MgO (including Irtran®, manufactured by International Crystal Laboratory of Garfield, N.J.), NaCl, Si (either pure or doped with materials, such as, for example, boron, to make the silicon a p-type semiconductor), a TlI-TlBr mixture (such as KRS-5® manufactured by Spectra-Tech, Stamford, Conn.), ZnS, ZnSe, optical glasses, sapphire, a-quartz, fused quartz, polyethylene, or polytetrafluoroethylene. If the optical window 4 is formed from a hard solid material, such as, for example, Ge, ZnSe and α-quartz, the optical window 4 is formed with a shape and size so that the optical window 4 will fit tightly within the upper section 2a of the bore 2 of frame 1 and so that the shoulder 3 prevents the optical window 4 from sliding out of the frame 1. In the embodiment of the present invention shown in FIGS. 1A and 1B, the optical window 4 has a square shape so that it fits tightly into the squared shaped upper section 2a of the bore 2. An adhesive or sealer may also be used to affix such an optical window 4 to the shoulder 3 to ensure that the optical window 4 provides a fluid-tight seal for the recess 5 so that liquid containing samples can be placed into the recess 5 for analysis. If the optical window 4 is formed from a powder of a soft material, such as, for example, AgCl, KBr and TlI-TlBr, the powder is introduced into the bore 2 and then compressed or molded to the shape of the upper portion 2a of the bore 2, with or without the application of heat, to form a solid optical window 4. The shoulder 3 in the bore 2 aids in locking such an optical window 4 into place. Alternatively, if the optical window 4 is made of a powder of a soft material, the optical window 4 may be molded into the appropriate shape and then inserted and affixed into the upper section 2a of the bore 2, or introduced as a powder into the bore 2 and then compressed. The upper surface of the optical window 4 forming the bottom of the recess 5 is planar or flat. Alternatively, the upper surface of the optical window 4 is randomly scratched, wedge-shaped or concave to substantially eliminate infrared interference fringes.

A flexible film 6 is preferably mounted to the upper surface 1a of the frame 1 so that only one edge of the film 6 is attached by an appropriate means, such as, for example, by the application of a line of an adhesive 7 or by heat fusion. The size and shape of the film 6 are such that the film 6 is substantially larger than the bore 2 so that the film 6 can completely cover the bore 2. The film 6 is made of a material that has a relatively low index of refraction and that is substantially transparent to the frequencies of the infrared light to be used by the spectrophotometer. The thickness of the film 6 is selected so that the film 6 is flexible, so that it will not tear during use of the sample holder, and so that the interference fringes produced when the film 6 is exposed to the infrared light generated by the spectrophotometer are weak and have a wavelength substantially higher than the infrared absorption spectra of the samples analyzed. Thus, the film 6 is preferably made of polyethylene or fluorinated polyethylene and has a thickness of from about 1.0 µm. to about 2.0 µm. If the film 6 is comprised of the same material as that comprising the optical window 4, then the upper surface of the optical window 4 is randomly scratched, wedge-shaped, or has a concave or cone shaped indentation therein.

Figure 1C:
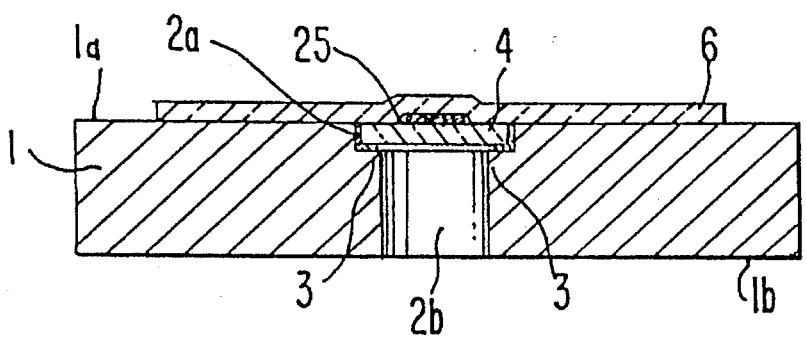
FIG. 1C is a cross-sectional side view of the embodiment of the present invention shown in FIG. 1A including a sample mounted on the sample holder.

In use, the film 6 is raised up and a sample 25 to be analyzed is placed onto the optical window 4. The film is then lowered to cover the sample 25 and the bore 2, as shown in FIG. 1C. The film 6 is then manually pressed down to contact the sample. When the sample to be analyzed is biological tissue or another soft and/or malleable material, the shape and thickness of the sample can be altered by manually pressing the film 6 and thus the sample. When the sample to be analyzed is a liquid or is liquid-containing, the liquid acts as a sealing agent between the film 6 and the upper surface 1a of the frame 1, thereby preventing any liquid from leaking or evaporating from the recess 5 in the sample holder during handling of the sample holder or during the infrared spectroanalysis. Because the film 6 is thin and flexible, it is not uniformly flat. As a consequence, the paths of propagation of adjacent infrared light rays are different in length, thereby substantially eliminating interference fringes in the infrared spectra of the sample and significantly clarifying the infrared absorption spectra of the sample being analyzed.

Figure 2:
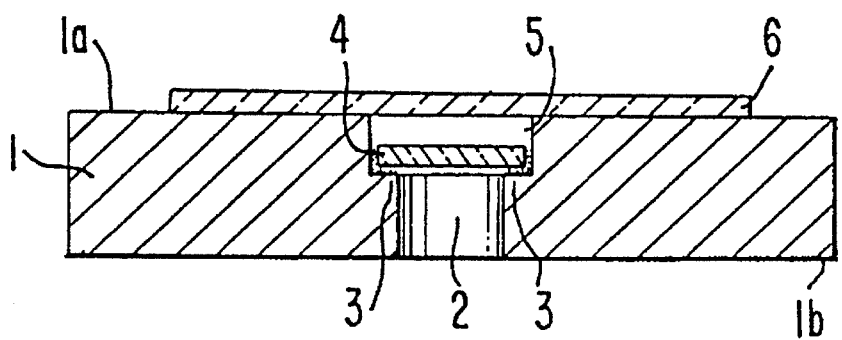
FIG. 2 is a cross-sectional side view of a second embodiment of the disposable all purpose micro sample holder of the present invention.

Referring to FIG. 2, a second embodiment of the present invention is shown in which the position and shape of the shoulder 3 and the thickness of the optical window 4 are selected so as to form a recess 5 between the upper surface of the optical window 4 and the upper surface 1a of frame 1. In use, a sample is placed on the optical window 4 in the recess 5 and the attached film 6 is then lowered to cover the sample and the optical window 4 and pressed down so as to contact and optionally reshape the sample to adjust so that the path length of the infrared light to pass through the sample is adjusted to substantially eliminate interference fringes.

Figure 3:
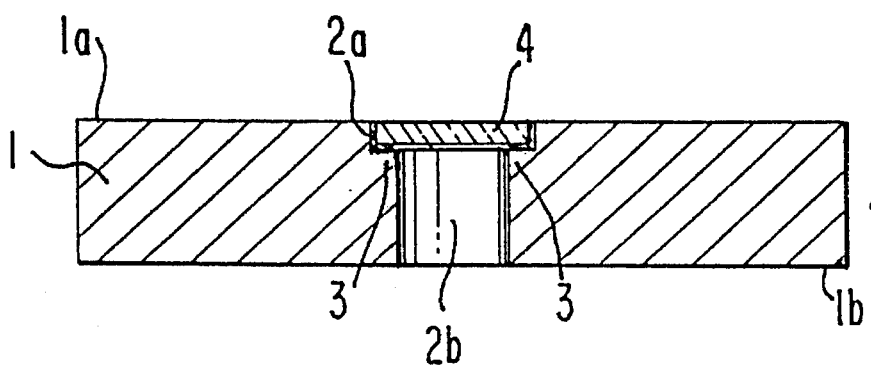
FIG. 3 is a cross-sectional side view of a third embodiment of the disposable all purpose micro sample holder of the present invention.

Although the film 6 is preferably attached to the upper surface 1a of the frame 1, the film 6 need not be attached. In this alternative embodiment, shown in FIGS. 3 and 4 for the sample holders shown in FIGS. 1A and 2 respectively, the film 6 is a separate element which is applied manually, with or without an adhesive, when or if needed. If the film 6 is not to be used at all, the upper surface of the optical window 4 is tapered to substantially eliminate infrared interference fringes of the sample being analyzed; alternatively, the upper surface of the optical window 4 may be randomly scratched or have a concave or cone shaped indentation therein.

Figure 5:
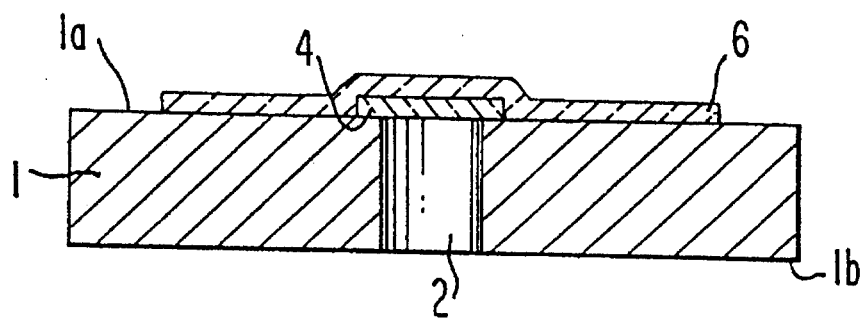
FIG. 5 is a cross-sectional side view of a fifth embodiment of the disposable all purpose micro sample holder of the present invention.

In the embodiment of the present invention shown in FIG. 5, the sample holder is identical to that shown in FIG. 1A except that the optical window 4 is securely attached onto the upper surface 1a of frame 1. In this embodiment, the optical window completely covers the bore 2, which has no recessed shoulder, and the film 6 completely covers the optical window 4.

Figure 6:
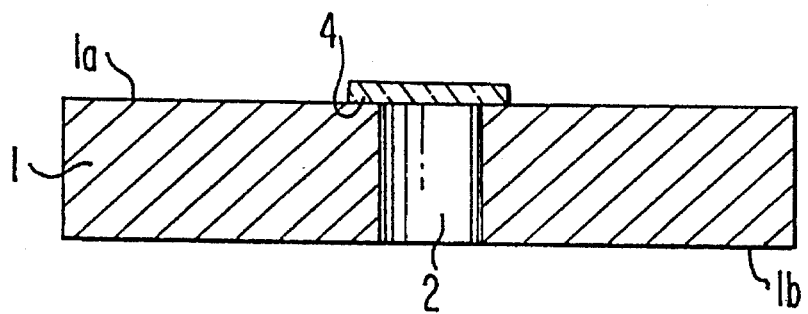
FIG. 6 is a cross-sectional side view of a sixth embodiment of the disposable all purpose micro sample holder of the present invention.

The embodiment of the present invention shown in FIG. 6, is identical to that shown in FIG. 5 except that the film 6 is not affixed to the sample holder.

Figure 7:
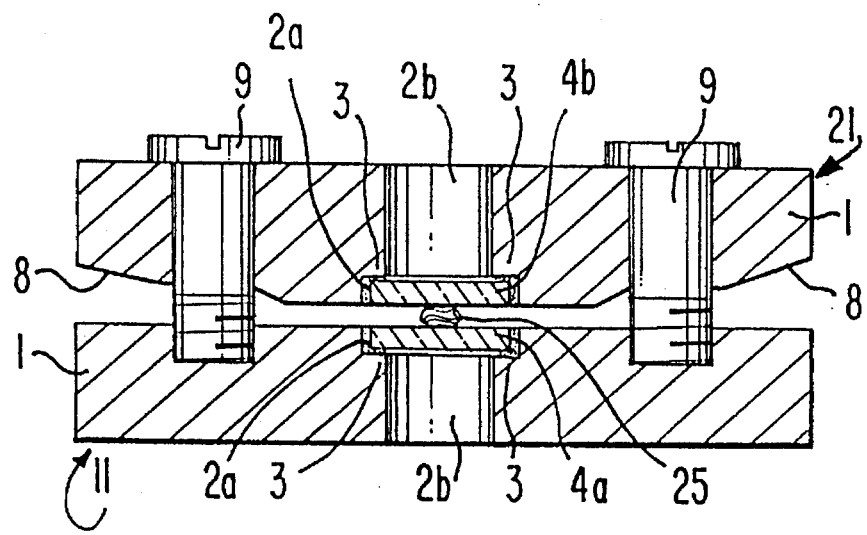
FIG. 7 is a cross-sectional side view of a seventh embodiment of the disposable all purpose micro sample holder of the present invention.

When a sample to be analyzed is in powder or solid form, it also may be analyzed in another embodiment of the sample holder of the present invention shown in FIG. 7. In this embodiment, two sample holders 11 and 21 are clamped together and the film 6 is not required. The bottom sample holder 11 is substantially identical to that shown in FIG. 3, except that two threaded screw bores are formed into the frame 1 adjacent to the central bore 2. The upper sample holder 21 is substantially identical to the bottom sample holder 11 and similarly has two screw bores, which need not be threaded, formed into the frame 1 adjacent to the central bore 2. Two screws 9 are used to releasably clamp the two sample holders 11, 21 together so that the bores 2 of the two sample holders 11, 21 are substantially coaxial and so that the bottom surface of the upper sample holder 21 abuts the upper surface of the lower sample holder 11. Alternatively, more than two screws 9 may be used to clamp the two sample holders together. Other clamping means known to those skilled in the art may alternatively be used to releasably clamp the two sample holders 11, 21 together with a constant pressure or with a pressure that is varied during the spectroanalysis. The bottom surface 8 of the frame 1 of the upper sample holder 21 is preferably tapered to enable the screws 9 to provide additional clamping force which may also be angularly adjusted. Prior to clamping the upper sample holder 21 onto the lower sample holder 11, the powdered or solid sample 25 is placed onto the optical window 4a of the lower sample holder 11. Because the lower surface of the upper sample holder 21 is tapered, by varying the pressure exerted by the screws 9 to the two sample holders 11, 21, the thickness of the sample and/or the relative axial orientation of the two optical windows 4a, 4b may be changed to substantially eliminate interference fringes during infrared analysis of the sample. The material comprising the optical window 4a of the lower sample holder 11 may be the same as or different than that comprising the optical window 4b of the upper sample holder 21. Similarly, the material comprising the frames 1 of the two sample holders 11, 21 may be the same or different. By varying the clamping force applied to the sample 25 by the screws 9 or other clamping means, the double sample holder embodiment shown in FIG. 7 can be used to determine the pressure dependencies of the infrared absorption spectra of the sample 25.

Figure 4:
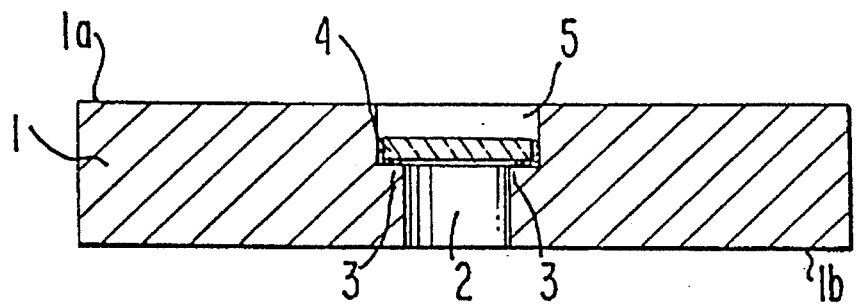
FIG. 4 is a cross-sectional side view of a fourth embodiment of the disposable all purpose micro sample holder of the present invention.

Alternatively, the lower sample holder 11 and/or the upper sample holder 21 may be substantially identical to the sample holder shown in FIG. 4 in which the optical window 4 is positioned in the frame 1 so that the upper surface of the optical window 4 is not flush with the upper surface 1a of the frame 1. In this embodiment, a recess is formed between the optical windows 4a, 4b of the two sample holders 11, 21 into which a sample may be placed. By properly selecting the positions and/or the thicknesses of the optical windows 4a, 4b in the central bores 2 of the frames 1, the size of the sample recess can be such that the two optical windows 4a, 4b can contact and exert a pressure upon the sample when the two sample holders 11, 21 are clamped together by the screws 9 or other clamping means. Consequently, pressure varying infrared spectral analysis can be performed in conjunction with this double sample holder embodiment.

Alternatively, the lower sample holder 11 and/or the upper sample holder 21 may be substantially identical to the sample holder shown in FIG. 6 in which the optical window 4 is affixed onto the surface of the frame 1 so that it completely covers the bore 2.

Figure 8A:
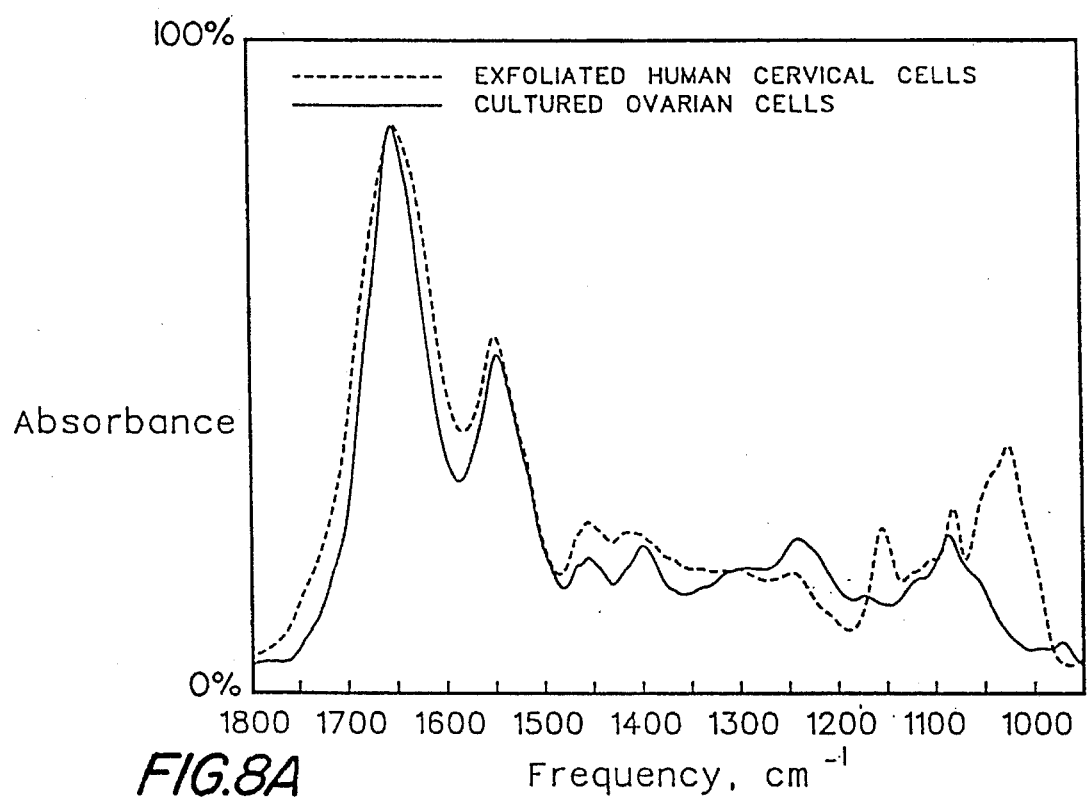
FIGS. 8A to 8J are graphical representations of infrared spectral data for various substances obtained using disposable all purpose micro sample holders of the present invention.
Figure 8B:
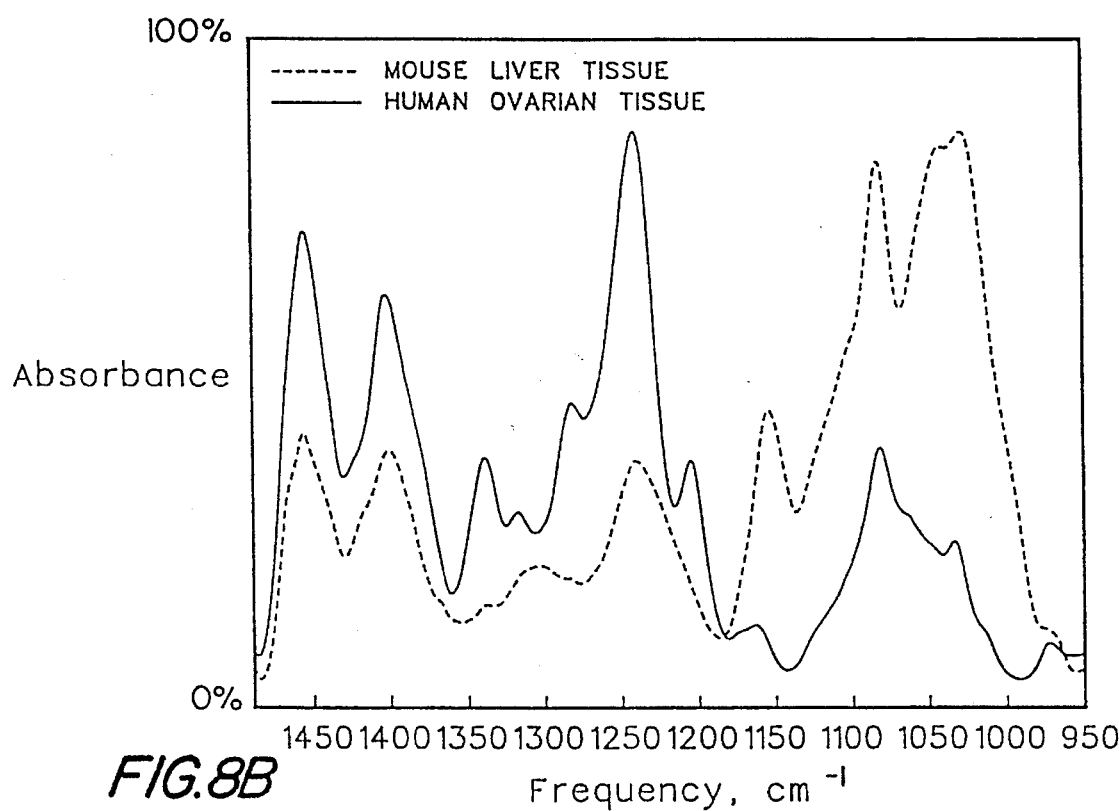
Figure 8C:
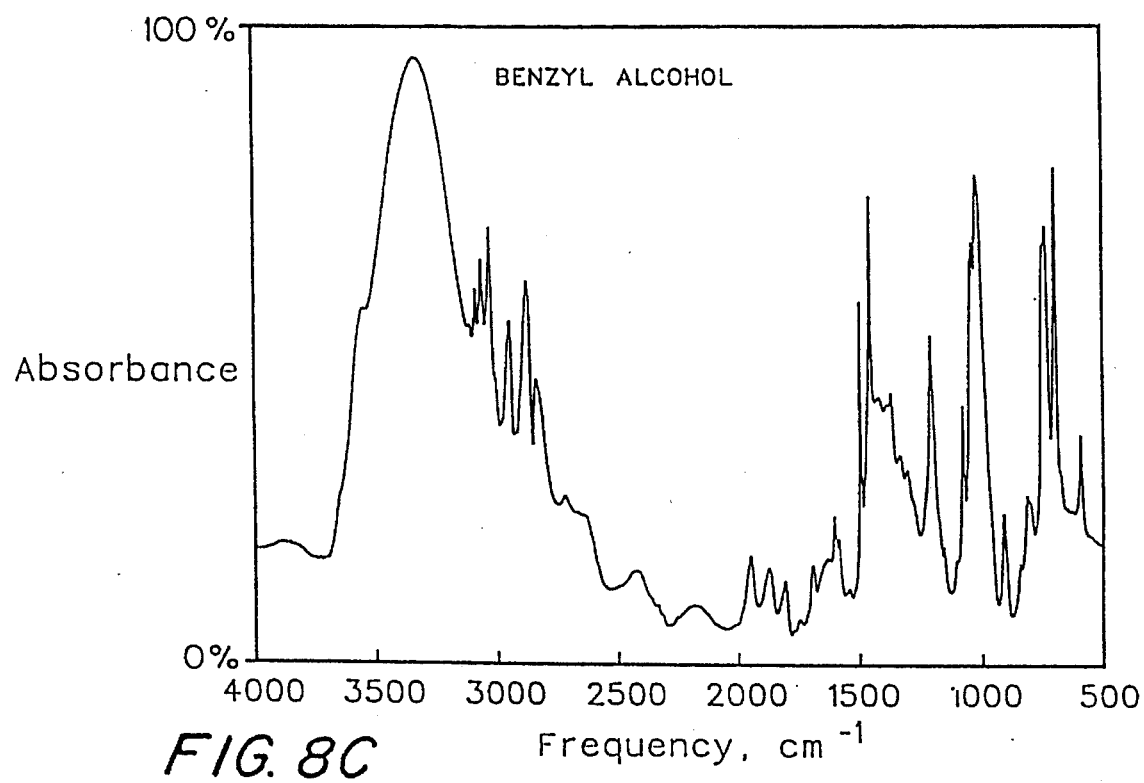
Figure 8D:
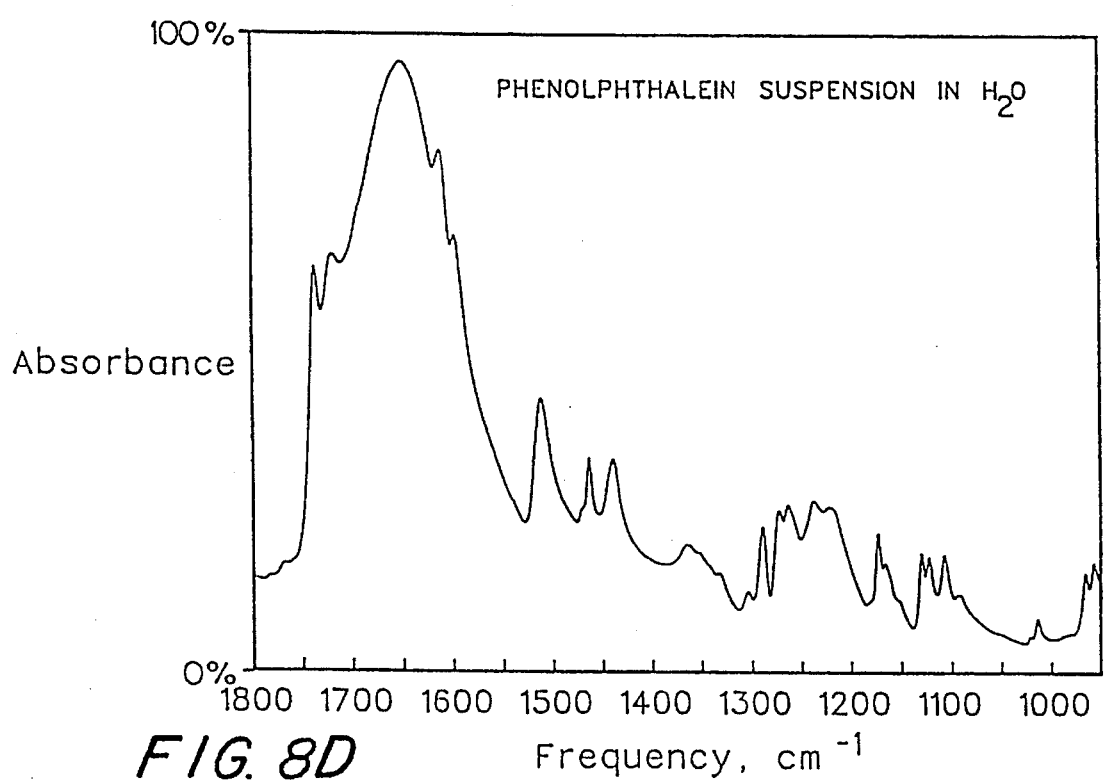
Figure 8E:
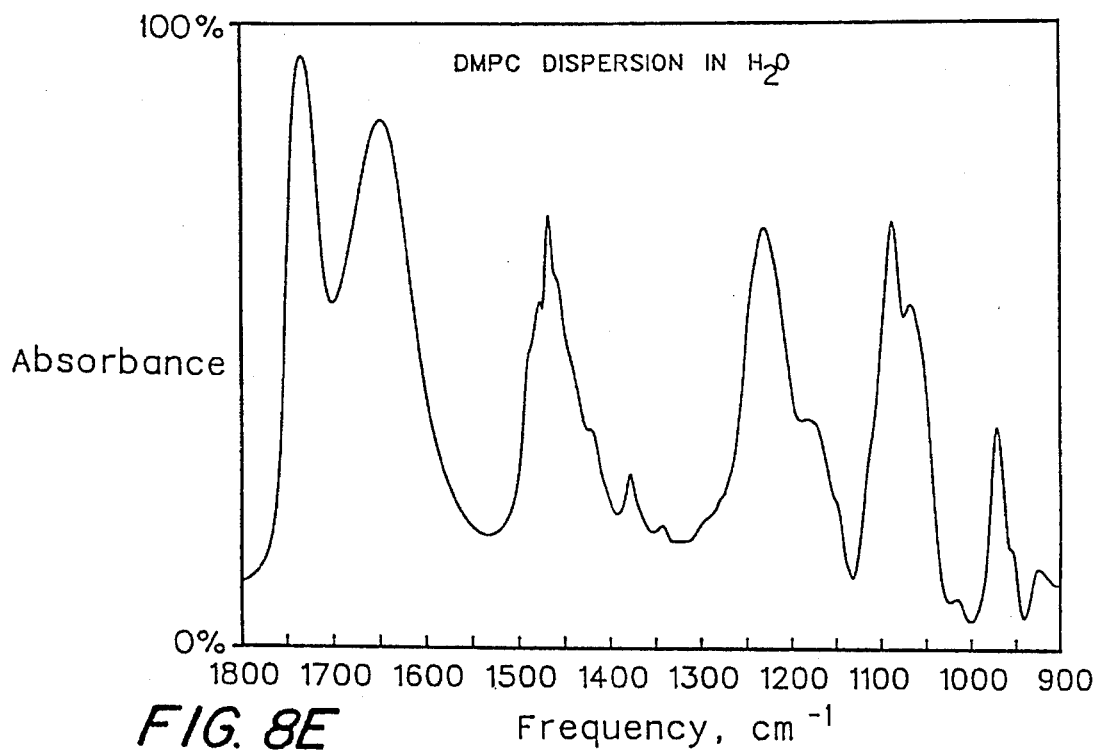
Figure 8F:
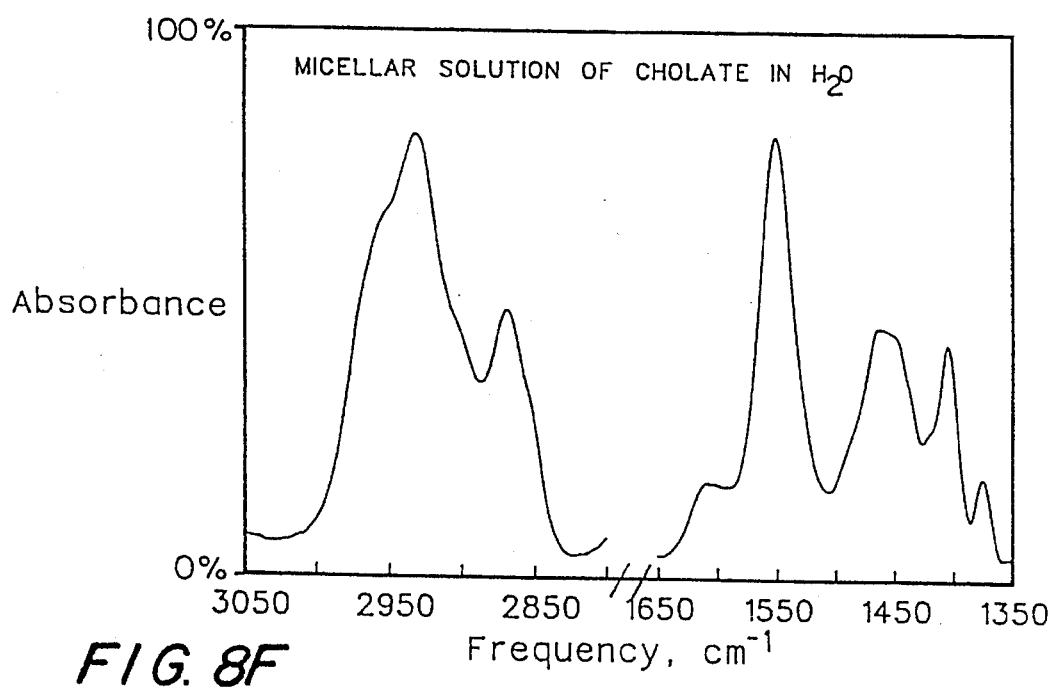
Figure 8G:
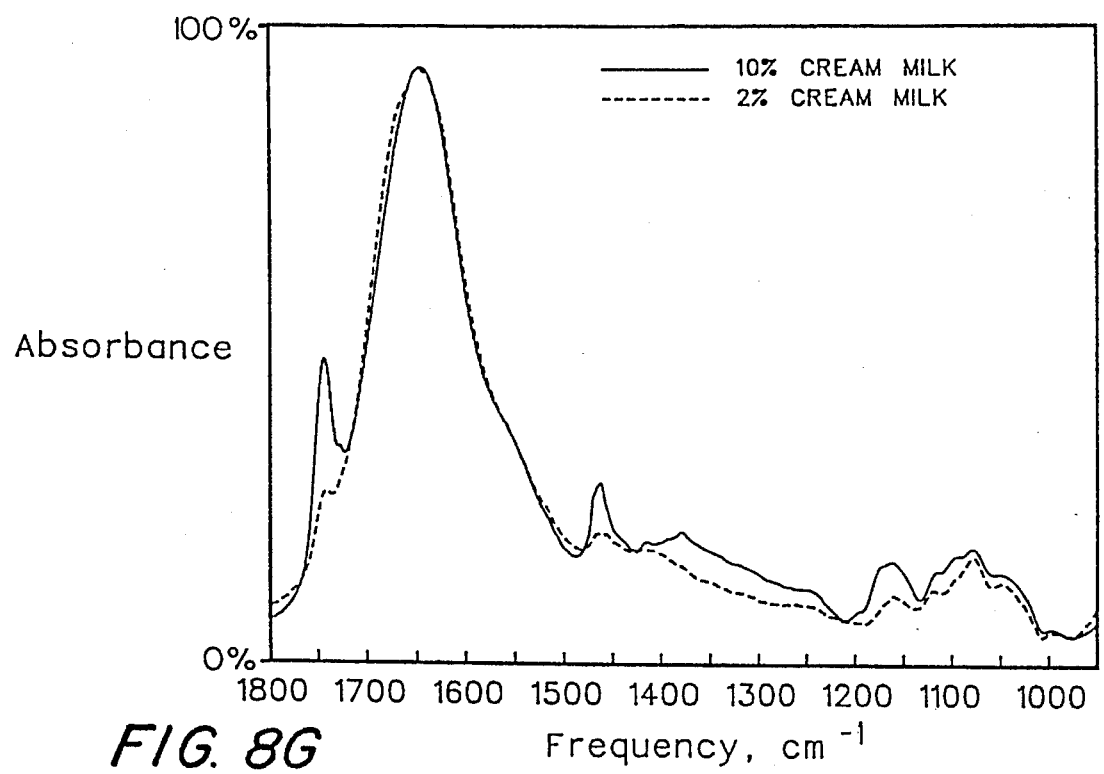
Figure 8H:
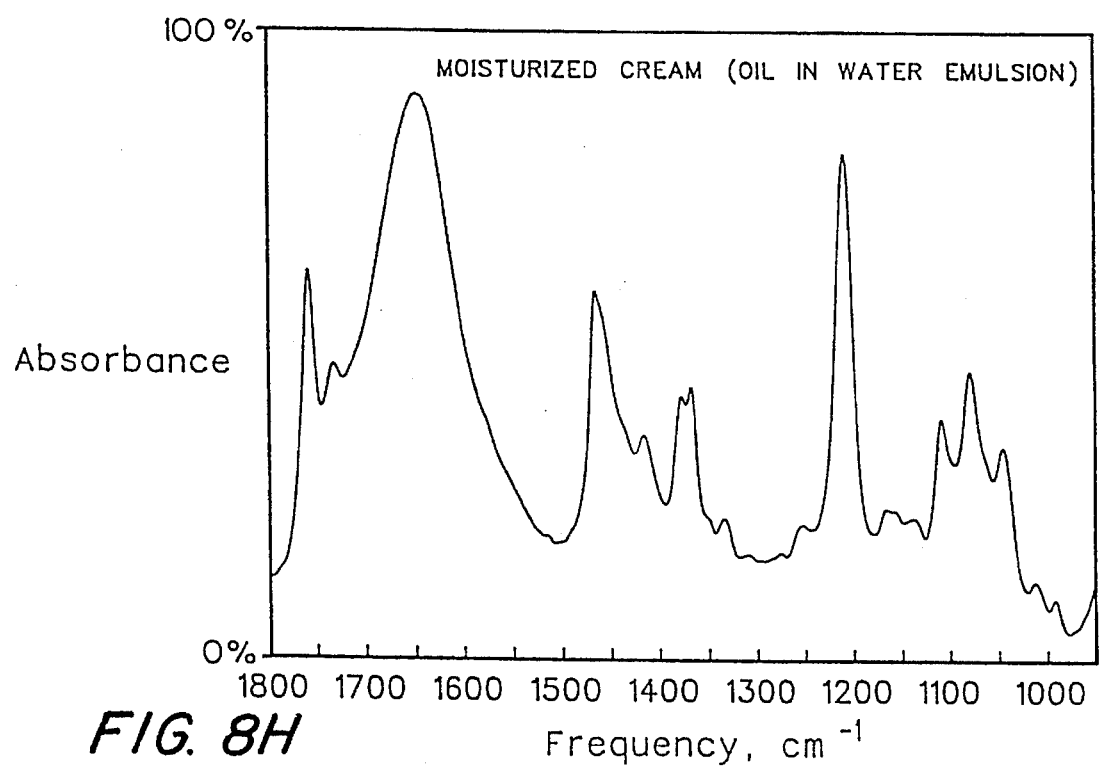
Figure 8I:
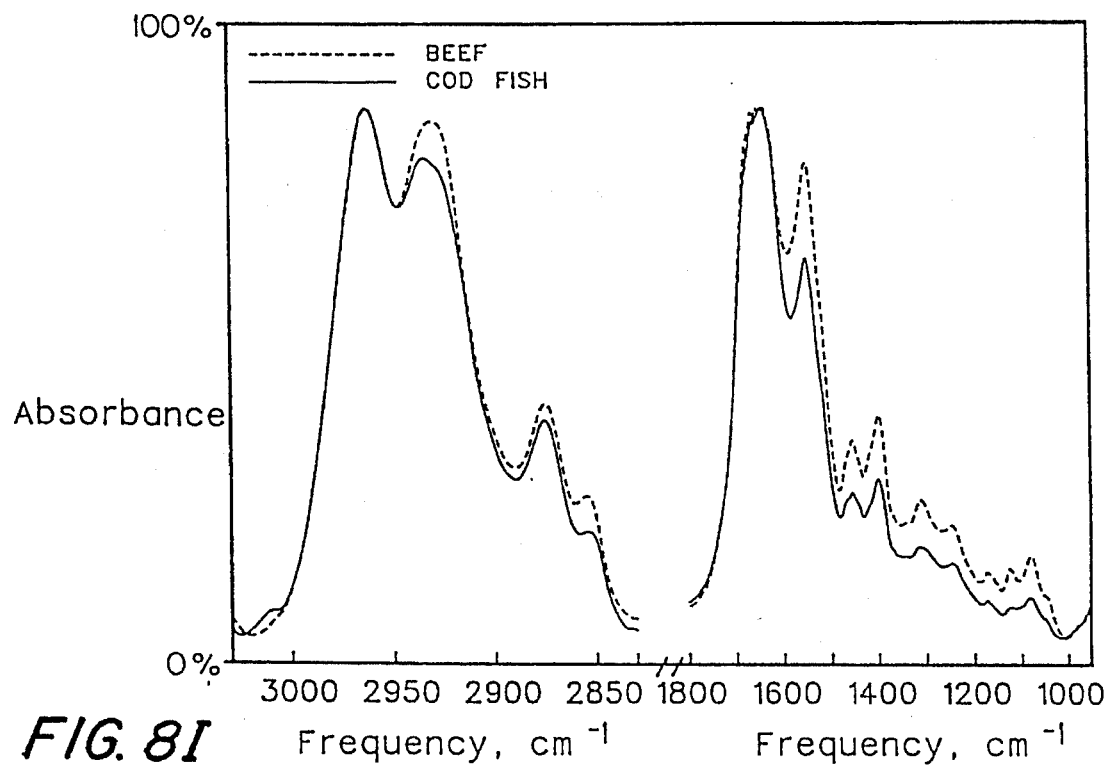
Figure 8J:
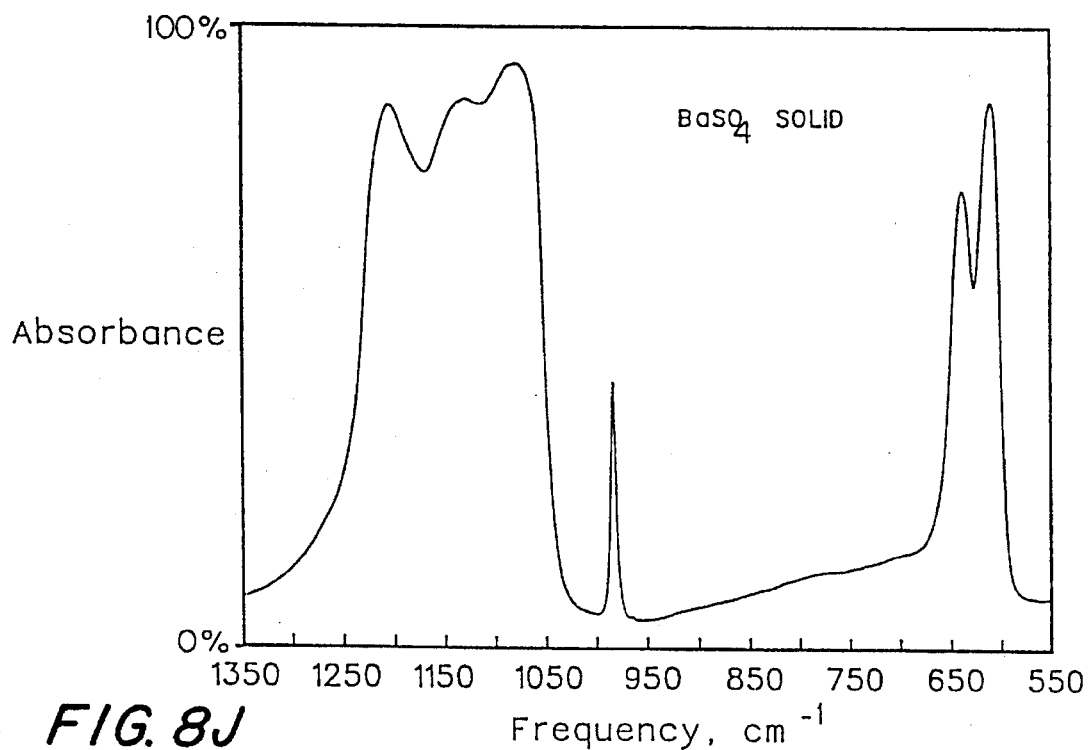

FIGS. 8A to 8J are graphical representations of infrared spectra of various substances obtained using the sample holder of the present invention, specifically exfoliated human cervical cells, cultured ovarian cells, mouse liver tissue, human ovarian tissue, benzyl alcohol, phenolphthalein suspension in water, 1,2-dimyristoylphosphatidylcholine (DMPC) dispersion in water, micellar solution of cholate in water, cream-milk mixtures, a moisturized cream (oil in water emulsion), beef tissue, cod fish tissue, and solid barium sulfate. The data shown in FIGS. 8A to 8J were obtained with a Nicolet Magna 550 Fourier-transform infrared spectrometer. For the biological cells and tissues, organic liquid, aqueous solutions, aqueous dispersion and suspension of solids and emulsion samples, data for which is shown in FIGS. 8A to 8H, a sample holder with a film was used as shown in FIGS. 1A and 1B. The frame was made of aluminum and had a thickness of 2 mm., was 5 cm. wide and 7.5 cm. long, and the central bore was 5 mm. in diameter. The window was made of silicon, had a thickness of 21 μm. The film was made of polyethylene and had a thickness of 1 μm. For the beef, cod fish and solid barium sulfate samples, the data for which is shown in FIGS. 8I to 8J, a sample holder as shown in FIG. 7 was used. Both frames were made of stainless steel and had a thicknesses of 2 mm., were circular with a 2.5 cm. diameter, and the central bores were 2.5 mm. in diameter. The windows were made of KRS-5®, had thicknesses of 1.5 mm., and no film was used.

Thus, while there have been shown and described and pointed out fundamental novel features of the invention as applied to preferred embodiments thereof, it will be understood that various omissions and substitutions and changes in the form and details of the disclosed apparatus, and in its operation, may be made by those skilled in the art without departing from the spirit of the invention. It is the intention, therefore, to be limited only as indicated by the scope of the claims appended hereto. For example, to enhance its infrared absorption spectrum characteristics, the sample to be analyzed may contain supplementary ingredients, such as, for example, $D_2O$ to remove the infrared absorption band of water and internal pressure calibrants such as α-quartz, $BaSO_4$ and deuterated water (HOD).

What is claimed is:

1. An infrared absorption spectra recording sample holder comprising:

a rigid frame substantially planar in shape having a bore passing from a first surface to a second surface thereof, said frame being substantially opaque to infrared light to be used in spectroanalysis of a sample and substantially unreactive to the sample to be analyzed;

an optical window having a size and shape and being mounted to said frame so as to cover the bore, said optical window being comprised of a material substantially transparent to the infrared light to be used in the spectroanalysis of the sample; and a flexible film having a size and shape and being mounted to said first surface of said frame so as to cover the bore, said film being comprised of a material substantially transparent to the infrared light to be used in the spectroanalysis of the sample.

2. The infrared absorption spectra recording sample holder of claim 1, wherein the infrared light to be used in the spectroanalysis of the sample has frequencies from about 10 to about 10,000 $cm^{-1}$ (wavelengths about 1 to about 1000 μm.).

3. The infrared absorption spectra recording sample holder of claim 1, wherein said optical window is comprised of at least one material selected from the group consisting of AgBr, AgCl, $BaF_2$, $CaF_2$, CsBr, CsI, Ge, KBr, KCl, LiF, $MgF_2$, MgO, NaCl, Si, p-type Si, a TlI-TlBr mixture, ZnS, ZnSe, optical glasses, sapphire, α-quartz, fused quartz, polyethylene, and polytetrafluoroethylene.

4. The infrared absorption spectra recording sample holder of claim 1, wherein said optical window is mounted within the bore of said frame so as to form a recess proximate to said first surface of said frame.

5. The infrared absorption spectra recording sample holder of claim 1, wherein said optical window is mounted within the bore of said frame so that a surface of said optical window is flush with said first surface of said frame.

6. The infrared absorption spectra recording sample holder of claim 1, wherein said optical window is mounted on said first surface of said frame.

7. The infrared absorption spectra recording sample holder of claim 1, wherein said flexible film has a thickness of between 1.0 μm. and 2.0 μm.

8. An infrared absorption spectra recording sample holder comprising:

a rigid frame substantially planar in shape having a bore passing from a first surface to a second surface thereof, said frame being substantially opaque to infrared light to be used in spectroanalysis of a sample and substantially unreactive to the sample to be analyzed;

an optical window having a size and shape and being mounted to said frame so as to cover the bore, said optical window being comprised of a p-type Si.

9. The infrared absorption spectra recording sample holder of claim 8, wherein the infrared light to be used in the spectroanalysis of the sample has frequencies from about 10 to about 10,000 $cm^{-1}$ (wavelengths about 1 to about 1000 μm.).

10. The infrared absorption spectra recording sample holder of claim 8, wherein said optical window is formed of solid p-type silicon.

11. The infrared absorption spectra recording sample holder of claim 8, wherein said optical window is mounted within the bore of said frame so as to form a recess proximate to said first surface of said frame.

12. The infrared absorption spectra recording sample holder of claim 8, wherein said optical window is mounted within the bore of said frame so that a surface of said optical window is flush with said first surface of said frame.

13. The infrared absorption spectra recording sample holder of claim 8, wherein said optical window is mounted on said first surface of said frame.

14. An infrared absorption spectra recording sample holder comprising:

a first bottom rigid frame substantially planar in shape having a first bore passing from a first surface to a second surface thereof, said first frame being substantially opaque to infrared light to be used in spectroanalysis of a sample and substantially unreactive to the sample to be analyzed;

a first optical window having a size and shape and being mounted to said first frame so as to cover the first bore, said first optical window being comprised of a material substantially transparent to the infrared light to be used in the spectroanalysis of the sample;

a second upper rigid frame substantially planar in shape having a second bore passing from a first surface to a second surface thereof, said second frame being substantially opaque to infrared light to be used in spectroanalysis of a sample and substantially unreactive to the sample to be analyzed;

a second optical window having a size and shape and being mounted to said second frame so as to cover the second bore, said second optical window being comprised of a material substantially transparent to the infrared light to be used in the spectroanalysis of the sample; and a clamping means for releasably clamping said first frame to said second frame so that said first bore is substantially coaxial with said second bore and so that said first surface of said first frame abuts said first surface of said second frame;

wherein said first optical window is mounted to said first frame and said second optical window is mounted to said second frame so that when said clamping means clamps said first and second frames together, said first and second optical windows contact a sample positioned therebetween.

15. The infrared absorption spectra recording sample holder of claim 14, wherein the infrared light to be used in the spectroanalysis of the sample has frequencies from about 10 to about 10,000 $cm^{-1}$ (wavelengths about 1 to about 1000 μm.).

16. The infrared absorption spectra recording sample holder of claim 14, wherein at least one of said first and second optical windows is comprised of at least one material selected from the group consisting of AgBr, AgCl, $BaF_2$, $CaF_2$, CsBr, CsI, Ge, KBr, KCl, LiF, $MgF_2$, MgO, NaCl, Si, p-type Si, a TlI-TlBr mixture, ZnS, ZnSe, optical glasses, sapphire, α-quartz, fused quartz, polyethylene, and polytetrafluoroethylene.

17. The infrared absorption spectra recording sample holder of claim 14, wherein at least one of said first and second optical windows is mounted within said first and second bores of said first and second frames so as to form a recess proximate to at least one of said first surfaces of said first and second frames.

18. The infrared absorption spectra recording sample holder of claim 14, wherein at least one of said first and second optical windows is mounted within said first and second bores of said first and second frames so that a surface of said first and second optical windows is flush with at least one of said first surfaces of said first and second frames.

19. The infrared absorption spectra recording sample holder of claim 14, wherein at least one of said first and second optical windows is mounted on at least one of said first surfaces of said first and second frames.

20. The infrared absorption spectra recording sample holder of claim 14, wherein said first surface of said second frame is tapered relative to said second surface of said second frame.

* * * * *